(12) United States Patent
Yu et al.

(10) Patent No.: US 9,527,837 B2
(45) Date of Patent: Dec. 27, 2016

(54) INHIBITORS OF EZH2

(71) Applicant: Eli Lilly and Company, Indianapolis, IN (US)

(72) Inventors: Kuo-Long Yu, Zionsville, IN (US); Deqi Guo, Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 14/955,074

(22) Filed: Dec. 1, 2015

(65) Prior Publication Data

US 2016/0159782 A1    Jun. 9, 2016

Related U.S. Application Data

(60) Provisional application No. 62/088,045, filed on Dec. 5, 2014.

(51) Int. Cl.
| C07D 401/14 | (2006.01) |
| A61K 31/44 | (2006.01) |
| C07D 409/14 | (2006.01) |

(52) U.S. Cl.
CPC ........... *C07D 409/14* (2013.01); *C07D 401/14* (2013.01)

(58) Field of Classification Search
None
See application file for complete search history.

(56) References Cited

U.S. PATENT DOCUMENTS

| 8,691,507 B2 | 4/2014 | Copeland et al. |
| 2013/0040906 A1 | 2/2013 | Kuntz et al. |

FOREIGN PATENT DOCUMENTS

| WO | 2004/074301 | 9/2004 |
| WO | 2011/140324 | 11/2011 |
| WO | 2011/140325 | 11/2011 |
| WO | 2012/005805 | 1/2012 |
| WO | 2012/034132 | 3/2012 |
| WO | 2012/068589 | 5/2012 |
| WO | 2012/075080 | 6/2012 |
| WO | 2012/118812 | 9/2012 |
| WO | 2012/142504 | 10/2012 |
| WO | 2012/142513 | 10/2012 |
| WO | 2013/039988 | 3/2013 |
| WO | 2013/049770 | 4/2013 |
| WO | 2013/067296 | 5/2013 |
| WO | 2013/067300 | 5/2013 |
| WO | 2013/067302 | 5/2013 |
| WO | 2013/075083 | 5/2013 |
| WO | 2013/075084 | 5/2013 |
| WO | 2013/078320 | 5/2013 |
| WO | 2013/120104 | 8/2013 |
| WO | 2013/155317 | 10/2013 |
| WO | 2013/155464 | 10/2013 |
| WO | 2013/173441 | 11/2013 |
| WO | 2014/049488 | 4/2014 |
| WO | 2014/062720 | 4/2014 |
| WO | 2014/097041 | 6/2014 |
| WO | 2014/100080 | 6/2014 |
| WO | 2014/100646 | 6/2014 |
| WO | 2014/100665 | 6/2014 |
| WO | 2014/107277 | 7/2014 |
| WO | WO 2014/177982 A1 * | 11/2014 |
| WO | 2015/004618 | 1/2015 |
| WO | 2015/077193 | 5/2015 |
| WO | 2015/077194 | 5/2015 |
| WO | 2015/104677 | 7/2015 |
| WO | 2015/195848 | 12/2015 |

\* cited by examiner

*Primary Examiner* — Zinna Northington Davis
(74) *Attorney, Agent, or Firm* — Tina M Tucker; Danica Hostettler

(57) ABSTRACT

The present invention relates to compounds that inhibit activity of the histone lysine N-methyltransferase, Enhancer of Zeste Homolog 2 (EZH2), pharmaceutical compositions comprising the compounds, and methods of using the compounds to treat cancer, such as hematologic and solid tumors.

5 Claims, No Drawings

INHIBITORS OF EZH2

The present invention relates to compounds that inhibit activity of the histone lysine N-methyltransferase, Enhancer of Zeste Homolog 2 (EZH2), pharmaceutical compositions comprising the compounds, and methods of using the compounds to treat cancer, such as hematologic and solid tumors.

EZH2 is an enzyme that in humans is encoded by the EZH2 gene, and is the catalytic component within polycomb repressive complex 2 (PRC2) that is responsible for the methylation of lysine 27 on histone 3 (H3K27) in chromatin. EZH2 overexpression is thought to promote cancer as a result of increases in histone methylation which silences the expression of tumor suppressor genes. The catalytic activity of EZH2 is mediated by a 130 amino acid Su(var)3-9, enhancer of zeste and trithorax (SET) domain, which provides the binding pockets for S-adenosylmethionine (SAM) cofactor and the lysine substrate residue. The core PRC2 complex is comprised of EZH2 and proteins EED (Embryonic Ectoderm Development), SUZ12 (Suppressor of zeste 12 homolog) and RbAp46/48 (also known as RBBP7/4), and can also include other protein such as JARID2 AEBP2 and Polycomblike (PCL)1/2/3.

In addition to overexpression of EZH2, increased H3K27 methylation can also arise due to mutations which increase the catalytic efficiency of EZH2, such as Y641N, A677G, and A678V. In addition, tumors that lack or are defective in chromatin remodeling protein SNF5 (also known as SMARCB1/INI1) can demonstrate increased methylation and repression by PRC2. It is also reported that levels of H3K27 methylation can be modulated in solid tumors through various signaling pathways, such as those involving VEGFR2 and PI3K/AKT.

EZH2 inhibitors are already known in the literature. See for example, WO2012/142504, WO2012/142513, WO2013/120104, WO2013/173441, and WO2014/177982.

There remains a need to provide alternative EZH2 inhibitors for treatment of cancer. Accordingly, the present invention provides certain inhibitors of EZH2 which may be useful for treating cancer.

The present invention provides a compound which is N-[(4,6-dimethyl-2-oxo-1,2-dihydropyridin-3-yl)methyl]-5-{[4-(3-methoxyazetidin-1-yl)cyclohexyl]ethyl}-4-methylthiophene-3-carboxamide:

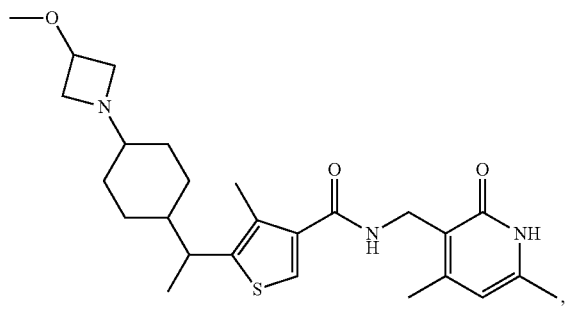

or a pharmaceutically acceptable salt thereof.

The present invention also provides a compound which is N-[(4,6-dimethyl-2-oxo-1,2-dihydropyridin-3-yl)methyl]-5-{1-[trans-4-(3-methoxyazetidin-1-yl)cyclohexyl]ethyl}-4-methylthiophene-3-carboxamide:

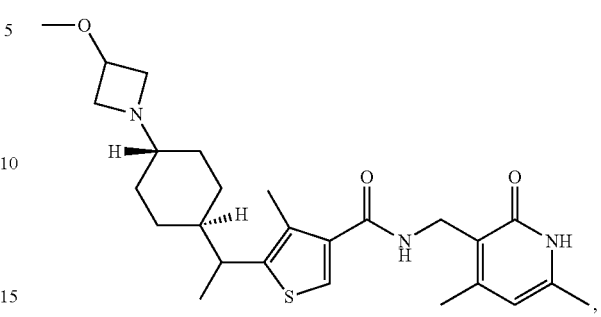

or a pharmaceutically acceptable salt thereof.

Preferably, the present invention provides a compound which is selected from the group consisting of N-[(4,6-dimethyl-2-oxo-1,2-dihydropyridin-3-yl)methyl]-5-{(1R)-1-[trans-4-(3-methoxyazetidin-1-yl)cyclohexyl]ethyl}-4-methylthiophene-3-carboxamide:

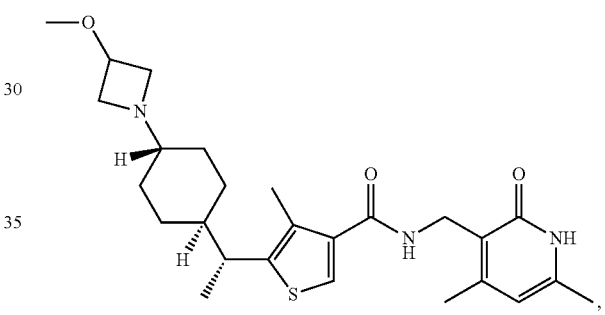

or a pharmaceutically acceptable salt thereof, and
N-[(4,6-dimethyl-2-oxo-1,2-dihydropyridin-3-yl)methyl]-5-{(1S)-1-[trans-4-(3-methoxyazetin-1-yl)cyclohexyl]ethyl}-4-methylthiophene-3-carboxamide:

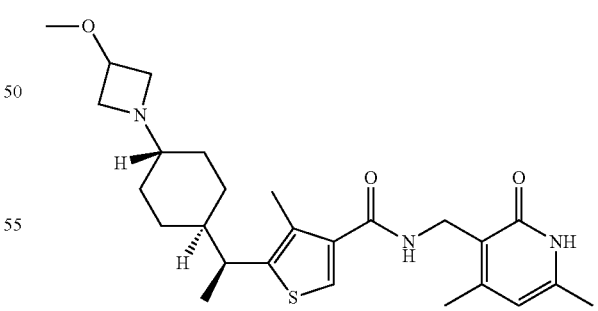

or a pharmaceutically acceptable salt thereof.

More preferably, the present invention provides a compound which is selected from the group consisting of N-[(4,6-dimethyl-2-oxo-1,2-dihydropyridin-3-yl)methyl]-5-{(1R)-1-[trans-4-(3-methoxyazetidin-1-yl)cyclohexyl]ethyl}-4-methylthiophene-3-carboxamide:

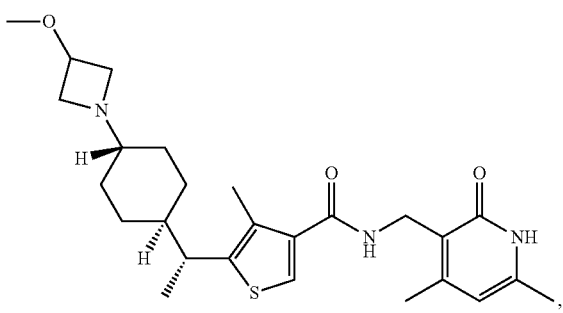

or a pharmaceutically acceptable salt thereof.

As a particular embodiment, the present invention provides a compound which is N-[(4,6-dimethyl-2-oxo-1,2-dihydropyridin-3-yl)methyl]-5-{(1R)-1-[trans-4-(3-methoxyazetidin-1-yl)cyclohexyl]ethyl}-4-methylthiophene-3-carboxamide.

As a particular embodiment, the present invention also provides a compound which is N-[(4,6-dimethyl-2-oxo-1,2-dihydropyridin-3-yl)methyl]-5-{(1S)-1-[trans-4-(3-methoxyazetin-1-yl)cyclohexyl]ethyl}-4-methylthiophene-3-carboxamide:

The present invention provides a method of treating cancer, preferably lymphomas, diffuse large B-cell lymphoma and, follicular lymphoma dependent on either activating mutant or wild-type EZH2, malignant and atypical teratoid rhabdoid tumors which lack or are defective for SNF5 (e.g. synovial sarcoma), glioblastoma, multiple myeloma, melanoma, gastrointestinal cancer, colorectal cancer, lung cancer, kidney cancer, breast cancer, ovarian cancer, and prostate cancer, comprising administering to a patient in need of such treatment an effective amount of a compound or salt of the present invention. Preferably the cancer is diffuse large B-cell lymphoma. Preferably the cancer is follicular lymphoma dependent on activating mutant or wild-type EZH2. Preferably the cancer is malignant and atypical teratoid rhabdoid tumor. Preferably the cancer is solid tumor which lacks or is defective for SNF5. Preferably the cancer is multiple myeloma. Preferably the cancer is gastric cancer. Preferably the cancer is ovarian cancer.

The present invention also provides a pharmaceutical composition comprising a compound or salt of the present invention, and one or more pharmaceutically acceptable excipients, carriers, or diluents.

This invention also provides a compound or salt of the present invention for use in therapy. Additionally, this invention provides a compound or salt of the present invention for use in the treatment of cancer, preferably lymphoma, diffuse large B-cell lymphoma, follicular lymphoma dependent on either activating mutant or wild-type EZH2, malignant and atypical teratoid rhabdoid tumor, solid tumor which lacks or is defective for SNF5 (e.g. synovial sarcoma), glioblastoma, multiple myeloma, gastrointestinal cancer, colorectal cancer, lung cancer, kidney cancer, breast cancer, ovarian cancer, and prostate cancer. Preferably the cancer is diffuse large B-cell lymphoma. Preferably the cancer is follicular lymphoma dependent on activating mutant or wild-type EZH2. Preferably the cancer is malignant and atypical teratoid rhabdoid tumor. Preferably the cancer is solid tumor which lacks or is defective for SNF5. Preferably the cancer is multiple myeloma. Preferably the cancer is gastric cancer. Preferably the cancer is ovarian cancer. Furthermore, this invention provides the use of a compound or a salt of the present invention in the manufacture of a medicament for treating cancer, preferably lymphoma, diffuse large B-cell lymphoma, follicular lymphoma dependent on either activating mutant or wild-type EZH2, malignant and atypical teratoid rhabdoid tumor, solid tumor which lacks or is defective for SNF5 (e.g. synovial sarcoma), glioblastoma, multiple myeloma, gastrointestinal cancer, colorectal cancer, lung cancer, kidney cancer, breast cancer, ovarian cancer, and prostate cancer. Preferably the cancer is diffuse large B-cell lymphoma. Preferably the cancer is follicular lymphoma dependent on activating mutant or wild-type EZH2. Preferably the cancer is malignant and atypical teratoid rhabdoid tumor. Preferably the cancer is solid tumor which lacks or is defective for SNF5. Preferably the cancer is multiple myeloma. Preferably the cancer is gastric cancer. Preferably the cancer is ovarian cancer.

This invention also provides a compound or salt of the present invention for use in simultaneous, separate or sequential administration in combination with one or more chemotherapy agents or radiation in the treatment of cancer.

It will be understood by the skilled reader that a compound of the present invention is capable of forming salts. The compound of the present invention is a base, and accordingly reacts with any of a number of inorganic and organic acids to form pharmaceutically acceptable salts. Such pharmaceutically acceptable acid addition salts and common methodology for preparing them are well known in the art. See, e.g., P. Stahl, et al., HANDBOOK OF PHARMACEUTICAL SALTS: PROPERTIES, SELECTION AND USE, (VCHA/Wiley-VCH, 2008); S. M. Berge, et al., "Pharmaceutical Salts," *Journal of Pharmaceutical Sciences*, Vol 66, No. 1, January 1977.

A compound or salt of the present invention may be prepared by a variety of procedures known in the art, some of which are illustrated in the Preparations and Examples below. The specific synthetic steps described may be combined in different ways to prepare compounds or salts of the present invention. The products of synthetic steps can be recovered by conventional methods well known in the art, including extraction, evaporation, precipitation, chromatography, filtration, trituration, and crystallization. The reagents and starting materials are readily available to one of ordinary skill in the art.

Some intermediates or compounds of the present invention may have one or more chiral centers. The present invention contemplates all individual enantiomers or diastereomers, as well as mixtures of the enantiomers and diastereomers of said compounds including racemates. It is preferred that compounds of the present invention containing at least one chiral center exist as single enantiomers or diastereomers. The single enantiomers or diastereomers may be prepared beginning with chiral reagents or by stereoselective or stereospecific synthetic techniques. Alternatively, the single enantiomers or diastereomers may be isolated from mixtures by standard chiral chromatographic or crystallization techniques. The skilled artisan will appreciate that in some circumstances the elution order of enantiomers or diastereomers may be different due to different chromatographic columns and mobile phases.

Protection and deprotection conditions are well known to the skilled artisan and are described in the literature (See for example "*Greene's Protective Groups in Organic Synthesis*", Fourth Edition, by Peter G. M. Wuts and Theodora W. Greene, John Wiley and Sons, Inc. 2007).

Certain abbreviations are defined as follows: "ACN" refers to acetonitrile; "AdoMet" refers to S-adenosyl-L-methionine' "AEBP" refers to adipocyte-enhancer binding protein; "bid" refers ti twice a day dosing; "BSA" refers to Bovine Serum Albumin; "CDI" refers to 1,1'-carbonyldiimidazole; "Ci" refers to Curie; "CPM" refers to counts per million; "DMEA" refers to dimethylethylamine; "DMF" refers to dimethylformamide; "DMSO" refers to dimethyl sulfoxide; "DNase" refers to deoxyribonuclease; "DTT" refers to dithiothreitol; "EDCI" refers to 1-(3-dimethylaminopropyl)-3-ethylcarbodiimide hydrochloride; "ee" refers to enantiomeric excess; "EED" refers to embryonic ectoderm development; "EtOAc" refers to ethyl acetate; "EtOH" refers to ethanol or ethyl alcohol; "Ex" refers to example; "GAPDH" refers to glyceraldehyde 3-phosphate dehydrogenase; "HEC" refers to hydroxy ethyl cellulose; "HOAt" refers to 1-hydroxy-7-azobenzotriazole; "$^3$H-SAM" refers to adenosyl-L-methionine, S [methyl-$^3$H]; "IC$_{50}$" refers to the concentration of an agent that produces 50% of the maximal inhibitory response possible for that agent; "min" refers to minute or minutes; "IPA" refers to isopropyl alcohol or isopropanol; "LiHMDS" refers to lithium bis(trimethylsilyl) amide; "MeOH" refers to MeOH or methyl alcohol; "MTBE" refers to methyl tert-butyl ether; "mut" refers to mutant; "PBS" refers to Phosphate Buffered Saline; "PCR" refers to polymerase chain reaction; "Pd(OAc)$_2$" refers to palladium acetate; "PRC2" refers to Polycomb Repressive Complex 2" "Prep" refers to preparation; "RBBP4" refers to retinoblastoma binding protein 4; "RNase" refers to ribonuclease; "rpm" refers to revolutions per minute; "R$_f$" refers to retention time in minutes; "SFC" refers to supercritical fluid chromatography; "SPA" refers to scintillation proximity assay; "THF" refers to tetrahydrofuran, "Tris" refers to tris(hydroxymethyl)aminomethane; "WT" refers to wild type; and "XPhos Pd Gen 2" refers to chloro(2-dicyclohexylphosphino-2',4',6'-triisopropyl-1,1'-biphenyl)[2-(2'-amino-1,1'-biphenyl)]palladium(II).

Preparation 1

1,4-Dioxaspiro[4.5]decane-8-carboxylic acid

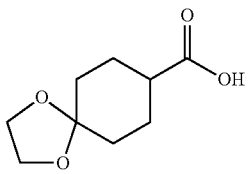 [SMILES: O=C(O)C1CCC2(CC1)OCCO2]

To a solution of ethyl 4-oxocyclohexanecarboxylate (900 g, 5.29 mol) in EtOH (4 L) add triethyl orthoformate (2.35 kg, 2.65 L, 15.9 mol) and p-toluenesulfonic acid (2.8 g, 16 mmol) and ethylene glycol (1.64 kg, 26.4 mol) and stir the mixture at 50° C. for 1 hour until disappearance of the starting ketone. Cool to 23° C. and slowly add over 20 minutes a 5 M aqueous solution of NaOH (4.24 L, 21.18 mol) and stir for 2 hours. Evaporate most of the EtOH and add water (5 L) and MTBE (4 L), stir, separate phases, and discard the organic phase. Cool to aqueous phase to 15° C. and acidify by slow addition of 5 M aqueous hydrochloric acid until pH~3.3 (approximately 3.7 L). Add CH$_2$Cl$_2$ (8 L) and dry the organic phase over Na$_2$SO$_4$, and evaporate to give the title compound as a viscous oil that slowly solidifies on standing as a white low-melting solid (887 g, 4.76 mol,  90%) that is used in the next step without further purification. (GC/MS) (m/z): 99 (M-87).

Preparation 2

N-Methoxy-N-methyl-1,4-dioxaspiro[4.5]decane-8-carboxamide

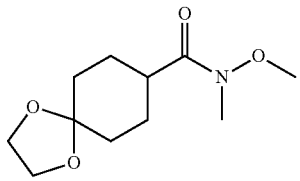 [SMILES: CON(C)C(=O)C1CCC2(CC1)OCCO2]

Add CDI (915 g, 5.64 mol) slowly in small portions over 20 minutes to a solution of 1,4-dioxaspiro[4.5]decane-8-carboxylic acid (988.6 g, 5.31 mol) in CH$_2$Cl$_2$ (10 L) while observing strong CO$_2$ gas evolution and stir for 1 hour. Add N-methoxymethanamine hydrochloride (577 g, 5.92 mol) in small portions over 15 minutes and stir for 12 hours. Add additional N-methoxymethanamine hydrochloride (53 g, 0.55 mol) and stir for an additional 12 hours. Add water (10 L), separate phases, and collect the organic layer. Wash the organic phase with water (5 L) and saturated aqueous sodium chloride (5 L), dry over Na$_2$SO$_4$, filter and evaporate to give the crude title compound as a colorless oil (1.24 kg, 102%) that is used without further purification. ES/MS (m/z): 230 (M+H).

Preparation 3

1-(1,4-Dioxaspiro[4.5]dec-8-yl)ethanone

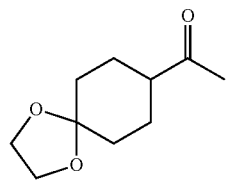

Cool a solution of N-methoxy-N-methyl-1,4-dioxaspiro[4.5]decane-8-carboxamide (400 g, 1.74 mol) in THF (3.5 L) under N$_2$ to 0° C. and add a 3 M CH$_3$MgBr in diethylether solution (697.87 mL, 2.1 mol) over 30 minutes. Stir for 30 minutes while warming to 23° C. Quench the reaction by slow addition of a saturated aqueous solution of NH$_4$Cl (1 L) and extract with MTBE (500 mL×3). Wash the organic extracts with saturated aqueous sodium chloride, dry over Na$_2$SO$_4$, filter, and evaporate to give the crude title compound as a light yellow oil (275 g, 86%) which is used without further purification. GC/MS (m/z): 86.1, 99.1.

Preparation 4

1-(1,4-Dioxaspiro[4.5]dec-8-yl)ethenyl diphenyl phosphate

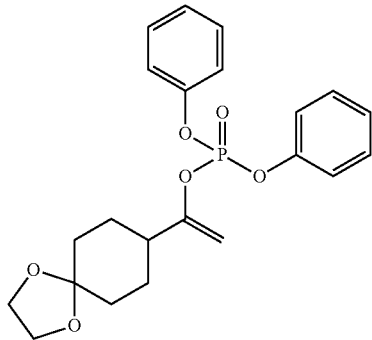 [SMILES: C=C(OP(=O)(Oc1ccccc1)Oc1ccccc1)C1CCC2(CC1)OCCO2]

Cool a solution of 1-(1,4-dioxaspiro[4.5]dec-8-yl)ethanone (150 g, 0.81 mol) in THF (1 L) to −70° C. and add drop wise 1 M LiHMDS in THF (896 mL, 0.89 mol) over 30 minutes. Stir the mixture 15 minutes at −60° C. and then add diphenyl phosphorochloridate (240.6 g, 896 mmol) drop wise in THF (450 mL) at −70° C. Stir the reaction mixture for 14 hours while warming to 20° C. Quench the reaction with a saturated aqueous solution of NaHCO₃ (1 L) and stir for 1 hour. Extract with MTBE (8 L×3), dry the organic phase over Na₂SO₄, filter, and evaporate. Purify the crude material by silica gel chromatography, eluting with hexanes:EtOAc 50:1 to 2:1 to give the title compound as a yellow oil (190 g, 56%). ES/MS (m/z): 417 (M+H).

Preparation 5

Methyl 4-methylthiophene-3-carboxylate

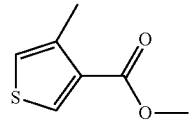

Dissolve 3-bromo-4-methyl-thiophene (1.00 kg, 5.65 mol) and triethylamine (1.43 kg, 14.12 mol) in N,N-dimethylacetamide (2.5 L) and MeOH (1.32 L) and add diphenylphophinoferrocene (187.9 g, 0.34 mol) and Pd(OAc)₂ (63.4 g, 0.28 mol). Stir the mixture under an atmosphere of CO at 50 psi at 80° C. for 16 hours. Cool the mixture to 23° C., add EtOAc (5 L), and wash with 10% aqueous citric acid (1.6 L×2), saturated aqueous NaHCO₃ (1.6 L×2), water (1.2 L×2) and saturated aqueous sodium chloride (1 L×2). Dry the organic phase over MgSO₄, filter, and evaporate to a residue. Purify the residue by silica gel chromatography eluting with 5% EtOAc in hexanes to give the title compound as a yellow oil (653 g, 74%). ES/MS (m/z): 157 (M+H).

Preparation 6

Methyl 4-methyl-5-(4,4,5,5-tetramethyl-1,3,2-dioxaborolan-2-yl)thiophene-3-carboxylate

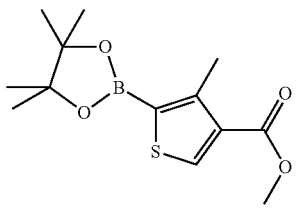 [SMILES: COC(=O)c1csc(B2OC(C)(C)C(C)(C)O2)c1C]

Mix methyl 4-methylthiophene-3-carboxylate (250 g, 1.60 mol), 4-tert-butyl-2-(4-tert-butyl-2-pyridyl)pyridine (8.59 g, 32.01 mmol) and bis(1,5-cyclooctadiene)di-μ-methoxydiiridium(I) (5.37 g, 8.00 mmol) in cyclohexane (2.5 L). Degas the mixture under vacuum and purge with N₂ (3×). Add 4,4,5,5-tetramethyl-1,3,2-dioxaborolane (409.67 g, 3.20 mol) in small portions over 1 hour and stir the resulting mixture at 70° C. for 3 hours. Cool the mixture to 23° C. and evaporate the solvent under vacuum. Purify the crude material by silica gel chromatography eluting with hexanes:EtOAc (200:1 to 100:1) to give the title compound as a solid (300 g, 66%). ES/MS (m/z): 283 (M+H).

Preparation 7

Methyl 5-[1-(1,4-dioxaspiro[4.5]dec-8-yl)ethenyl]-4-methylthiophene-3-carboxylate

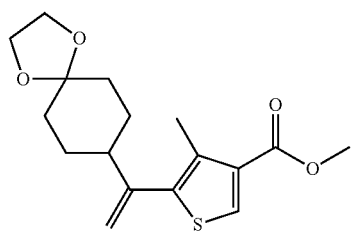 [SMILES: C=C(c1scc(C(=O)OC)c1C)C1CCC2(CC1)OCCO2]

Stir a mixture of 1-(1,4-dioxaspiro[4.5]dec-8-yl)ethenyl diphenyl phosphate (240 g, 576.37 mmol), methyl 4-methyl-5-(4,4,5,5-tetramethyl-1,3,2-dioxaborolan-2-yl)thiophene-3-carboxylate (211.4 g, 749.28 mmol) and K₃PO₄ (367 g, 1.73 mol, 2 M in water) in dioxane (2.4 L) at 23° C. Add XPhos Pd Gen 2 (9.07 g, 11.53 mmol) and stir at 80° C. for 3 hours. Evaporate the organic solvent at reduced pressure and extract with EtOAc (750 mL×2). Wash the organic extract with water (150 mL), dry over Na₂SO₄, filter, and evaporate to dryness. Purify the crude material by silica gel chromatography eluting with 5% EtOAc in hexanes to give title compound as a solid (375 g, 67%). ES/MS (m/z): 323 (M+H).

Preparation 8

Methyl 5-[(1R)-1-(1,4-dioxaspiro[4.5]dec-8-yl)ethyl]-4-methylthiophene-3-carboxylate

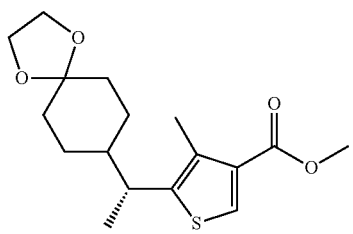

To a solution of methyl 5-[1-(1,4-dioxaspiro[4.5]dec-8-yl)ethenyl]-4-methylthiophene-3-carboxylate (60 g, 186 mmol) in CH$_2$Cl$_2$ (1.86 L), add ((4R,5R)-(+)-O-[1-benzyl-1-(5-methyl-2-phenyl-4,5-dihydrooxazol-4-yl)-2-phenylethyl](dicyclohexylphosphinite)(1,5-cyclooctadiene)iridium(I) tetrakis(3,5-bis(trifluoromethyl)phenylborate (1.61 g, 0.93 mmol) and elute the solution through a 48 mL stainless steel reactor with a hydrogen atmosphere of 80 par at 12 mL/minute at 23° C. until all of the solution is processed. Filter the solution and evaporate to dryness to give the crude title compound as a brown oil (60 g, quantitative yield) with no further purification. ES/MS (m/z): 325 M+H).

Preparation 9

Racemic Methyl 5-[1-(1,4-dioxaspiro[4.5]dec-8-yl)ethyl]-4-methylthiophene-3-carboxylate

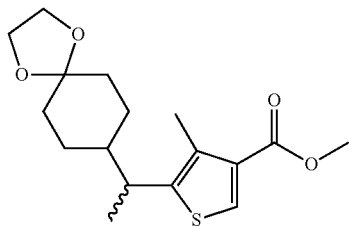 [SMILES: COC(=O)c1csc(C(C)C2CCC3(CC2)OCCO3)c1C]

Charge a stainless steel autoclave vessel with methyl 5-[1-(1,4-dioxaspiro[4.5]dec-8-yl)ethenyl]-4-methylthiophene-3-carboxylate (22.6 g, 70.1 mmol), EtOH (226 mL), EtOAc (68 mL) and triethylamine (24.4 mL). Add 10% Pd/C wet paste (2.26 g) and fit autoclave head. Purge with hydrogen then refill with hydrogen to 1400 kPa. Stir at ambient temperature overnight. Filter through diatomaceous earth and concentrate the filtrate to give the title compound as a colorless oil (22.0 g, 96%). ES/MS (m/z): 325 (M+H).

Preparation 10

Methyl 4-methyl-5-[(1R)-1-(4-oxocyclohexyl)ethyl]thiophene-3-carboxylate

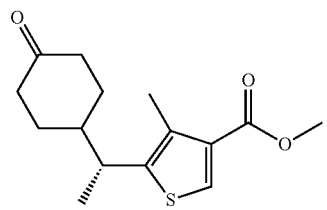 [SMILES: COC(=O)c1csc([C@H](C)C2CCC(=O)CC2)c1C]

Add to a solution of methyl 5-[(1R)-1-(1,4-dioxaspiro[4.5]dec-8-yl)ethyl]-4-methylthiophene-3-carboxylate (64.7 g, 178 mmol) in THF (450 mL), 1 N HCl (450 mL, 5.53 mol) and stir for 16 hours at 23° C. and at 45° C. for 2 hours. Evaporate the organic solvent, add MTBE (500 mL) and separate phases. Wash the organic phase with water (200 mL), saturated aqueous NaHCO$_3$ (100 mL) and saturated aqueous sodium chloride (100 mL), dry over MgSO$_4$, filter, and evaporate to dryness to give the crude title compound as a brown oil (53.3 g, 96%) which is used without further purification. ES/MS (m/z): 281 (M+H).

Prepare the following compound essentially by the method of Preparation 10 with the following changes. Stir the reaction mixture for 16 hours at 23° C. Add MTBE and separate phases. Work-up is completed as per Preparation 10 and purify the material by silica gel chromatography eluting with hexanes/MTBE 10-30%.

TABLE 1

| Prep No. | Chemical name | Structure | ES/MS (m/z) |
|---|---|---|---|
| 11 | Racemic Methyl 4-methyl-5-[1-(4-oxocyclohexyl)ethyl]thiophene-3-carboxylate | 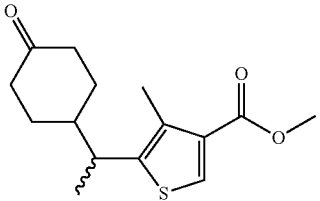 | 281 (M + 1) |

Preparation 12

Methyl 5-[(1R)-1-[trans-4-(3-methoxyazetidin-1-yl)cyclohexyl]ethyl]-4-methylthiophene-3-carboxylate

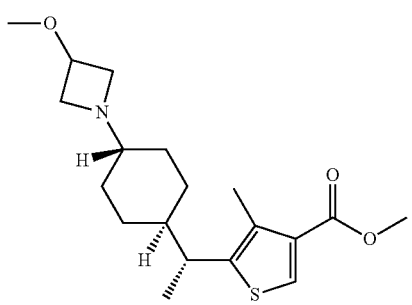

Stir a solution of 3-methoxyazetidine hydrochloride (43.4 g, 351 mmol) and N,N-diisopropylethylamine (48.2, 65 mL, 373 mmol) in MeOH (500 mL) for 45 minutes at 23° C. Add this to a solution of methyl 4-methyl-5-[(1R)-1-(4-oxocyclohexyl)ethyl]thiophene-3-carboxylate (50.0 g, 160 mmol) in THF (250 mL) and stir 40 minutes at 23° C. Cool the mixture at −70° C. and add LiBH$_4$ (4.9 g, 220 mmol) in five portions over 25 minutes. Allow to stir for 4 hours while warming to −20° C. Pour the mixture slowly into a 1 M aqueous solution of hydrochloric acid (500 mL) and stir for 10 minutes. Evaporate most of the organic solvent, add CH$_2$Cl$_2$ (500 mL) and a 5 M aqueous K$_2$CO$_3$ solution to adjust the pH to 9. Extract the organic phase and wash the aqueous phase again with CH$_2$Cl$_2$ (250 mL). Combine organic extracts, wash with saturated aqueous sodium chloride, dry over MgSO$_4$, filter, and evaporate to dryness. Add EtOAc (50 mL) and evaporate again. Purify the crude material with silica gel chromatography, eluting with 20% EtOAc in 2% triethylamine/hexanes to give an oil. Dissolve the oil in MTBE (200 mL), wash with aqueous 1 M hydrochloric acid (200 mL) and add aqueous 2 M K$_3$PO$_4$ to the aqueous phase to adjust the pH to 7.5. Extract the solution with EtOAc (300 mL×2), dry over MgSO$_4$, filter, and evaporate to dryness to give title compound as a pale yellow oil (15.5 g, 57%). ES/MS (m/z): 352 (M+H).

Prepare the following compound essentially by the method of Preparation 12 with essentially the same work-up through extraction with CH$_2$Cl$_2$, wash with sodium chloride, dry over MgSO$_4$, filter, and evaporate to dryness to give the crude title compound of Preparation 13. The material is used without further purification.

Preparation 14

5-[(1R)-1-[trans-4-(3-Methoxyazetidin-1-yl)cyclohexyl]ethyl]-4-methylthiophene-3-carboxylic acid

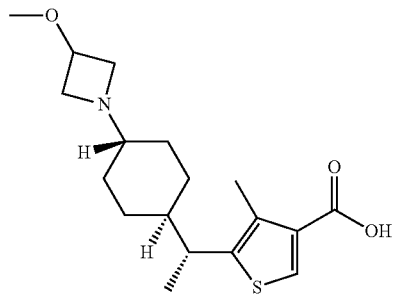 [SMILES: COC1CN([C@H]2CC[C@H]([C@@H](C)c3scc(C(=O)O)c3C)CC2)C1]

Add a solution of potassium hydroxide (15.1 g, 229 mmol) in 2-propanol (170 mL) to a solution of methyl 5-[(1R)-1-[trans-4-(3-methoxyazetidin-1-yl)cyclohexyl]ethyl]-4-methylthiophene-3-carboxylate (33.5 g, 90.5 mmol) in 2-propanol (170 mL) and stir the mixture at 80° C. for 2 hours. Cool the reaction with cold water and then add 4 M hydrochloric acid in 1,4-dioxane (57 mL, 228 mmol) in small portions over 30 minutes. After 15 minutes, evaporate all of the volatiles, dissolve the residue in THF and evaporate again. Dissolve the residue in THF, add heptane, and evaporate the volatiles to give the title compound as a white solid (30.5 g, quantitative). ES/MS (m/z): 338 (M+H).

Preparation 15

Racemic 5-{1-[trans-4-(3-Methoxyazetidin-1-yl)cyclohexyl]ethyl}-4-methylthiophene-3-carboxylic acid

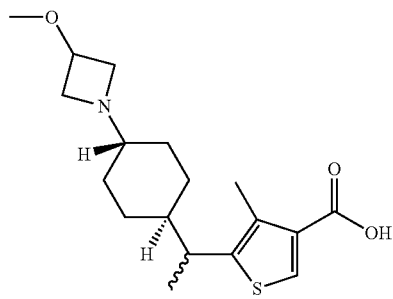 [SMILES: COC1CN([C@H]2CC[C@H](C(C)c3scc(C(=O)O)c3C)CC2)C1]

TABLE 2

| Prep No. | Chemical Name | Structure | ES/MS (m/z) |
|---|---|---|---|
| 13 | Racemica Methyl 5-{(1-[trans-4-(3-methoxyazetidin-1-yl)cyclohexyl]ethyl}-4-methylthiophene-3-carboxylate | 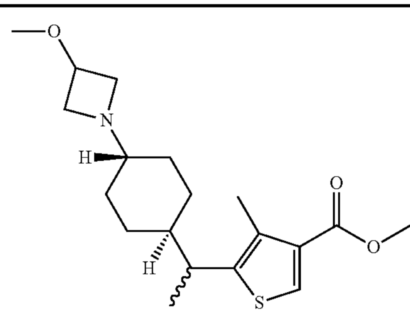 | 352 (M + H) |

Add a solution of potassium hydroxide (6.98 g, 106 mmol) in 2-propanol (140 mL) to a solution of racemic methyl 5-[1-[trans-4-(3-methoxyazetidin-1-yl)cyclohexyl]ethyl]-4-methylthiophene-3-carboxylate (17.58 g, 42.0 mmol) in 2-propanol (140 mL) and stir the mixture at 80° C. for 90 minutes. Cool the reaction with cold water and then add 4 M hydrochloric acid in 1,4-dioxane (26.3 mL, 99 mmol) over 5 minutes. Stir for 90 minutes, filter the solid through diatomaceous earth, wash the cake with IPA (150 mL) and CH$_2$Cl$_2$ (150 mL) and concentrate the cloudy filtrate. Add ACN (300 mL) and evaporate to a foam. Triturate with MTBE and evaporate to give the crude title compound as white solid (18.4 g, 75%) that is used without further purification. ES/MS (m/z): 338 (M+H).

EXAMPLE 1

N-[(4,6-Dimethyl-2-oxo-1,2-dihydropyridin-3-yl)methyl]-5-{(1R)-1-[trans-4-(3-methoxyazetidin-1-yl)cyclohexyl]ethyl}-4-methylthiophene-3-carboxamide

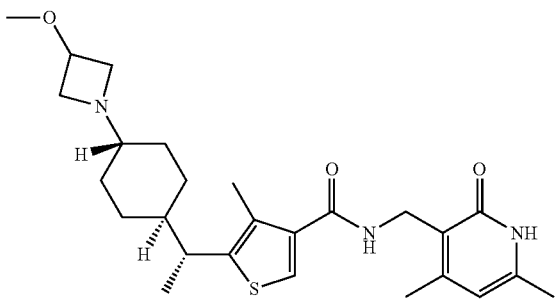

Add 3-(aminomethyl)-4,6-dimethylpyridin-2(1H)-one hydrochloride (25.8 g, 137 mmol) and N, N-diisopropylethylamine (65 mL, 373 mmol) to a suspension of 5-[(1R)-1-[trans-4-(3-methoxyazetidin-1-yl)cyclohexyl]ethyl]-4-methylthiophene-3-carboxylic acid (30.5 g, 90.5 mmol) in CH$_2$Cl$_2$ (400 mL) and stir the mixture for 30 minutes at 23° C. Add 1-(3-dimethylaminopropyl)3-ethylcarbodiimide hydrochloride (26.4 g, 138 mmol) and 1-hydroxybenzotriazole (3.65 g, 27.0 mmol) and stir at 23° C. for 16 hours. Add water (200 mL) and stir until all the solids dissolve. Separate the layers and wash the organic phase with water (200 mL), saturated aqueous sodium chloride (100 mL), dry over Na$_2$SO$_4$, filter (wash thoroughly with solvent), and evaporate to dryness. Purify the crude residue by silica gel chromatography eluting with 70/30 CH$_2$Cl$_2$/ACN to which 6% by volume of 2 M NH$_3$ in MeOH is added followed by 6% of 7 N NH$_3$ in MeOH. Combine the appropriate fractions and evaporate to dryness to give a soft off-white solid. Add acetone (400 mL) to the solid and stir for 1.5 hours, filter, and dry at 40° C. under vacuum to give the title compound (31.6 g, 72%). ES/MS (m/z): 472 (M+H), [α]$^{20}$$_D$-9.95 (c=1.0, MeOH), chiral analysis: CHIRALPAK® AD (4.6× 150 mm, 5 μM); EtOH (0.2% DMEA); 0.75 mL/min; uv=254 nM; R$_t$=6.97 min; >96% ee.

EXAMPLE 2

N-[(4,6-Dimethyl-2-oxo-1,2-dihydropyridin-3-yl)methyl]-5-{(1S)-1-[trans-4-(3-methoxyazetin-1-yl)cyclohexyl]ethyl}-4-methylthiophene-3-carboxamide

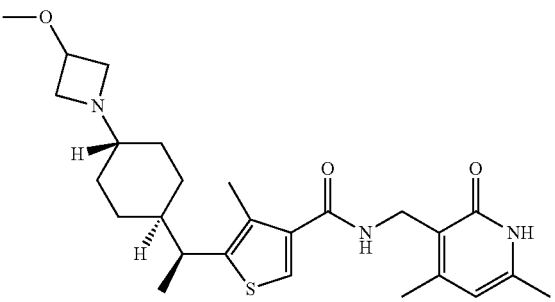

Add 3-(aminomethyl)-4,6-dimethylpyridin-2(1H)-one hydrochloride (40.3 g, 169 mmol) to a mixture of racemic 5-{1-[trans-4-(3-methoxyazetidin-1-yl)cyclohexyl]ethyl}-4-methylthiophene-3-carboxylic acid (55.0 g, 130 mmol), EDCI (55.0 g, 287 mmol) and HOAt (19.9 g, 143 mmol) in DMF (275 mL) and stir at 23° C. for 6 hours. Add water (800 mL) and stir the mixture for 30 minutes. Filter, collect the solid, and discard the filtrate. Partition the solid between EtOAc (500 mL) and water (800 mL) and add aqueous 1 M hydrochloric acid until pH=3. Separate the phases and discard the organic phase. Adjust the pH of the aqueous phase with aqueous 1 M sodium hydroxide until pH=8-9, filter the solid and discard the filtrate. Dissolve the solid in CH$_2$Cl$_2$, dry with MgSO$_4$, filter, and evaporate to dryness. Purify the crude material by silica gel chromatography eluting with a mixture of CH$_2$Cl$_2$/ACN 70/30 with 5% of 2 M ammonia in MeOH to give the racemic material (33 g, 54%). ES/MS (m/z): 472 (M+H). Collect the mixture fractions and heat in acetone (250 mL) at 50° overnight. Cool to room temperature, filter the solid, and dry under vacuum at 45° C. to give a solid which is purified by silica gel chromatography eluting with a mixture of CH$_2$Cl$_2$/ACN 70/30 with 5% of 2 M ammonia in MeOH. Crystallize the isolated material in hot acetone to give racemic material (4.5 g) and combine the isolated lots of racemic material (37.5 g, 60.8%). ES/MS (m/z): 472 (M+H). Separate the racemic material by SFC chiral chromatography using the following conditions: Column: CHIRALPAK® AD 5 μm, 5×25 cm, mobile phase: CO$_2$ with 35% EtOH (2% DMEA), flow rate of 250 g/minute, UV 254 mn with analytical conditions of SFC Chiralpck Ad (4.6×5 μm), mobile phase 35% EtOH (0.2% DMEA) in CO$_2$, 2.5 mL/min, 100 bar outlet pressure at 40° C. to give Example 1 (12.7 g, 21%, R$_t$=2.35 minutes, 94% ee) and Example 2 (8.7 g, 14%, R$_t$=2.86 minutes, 88% ee). ES/MS (m/z): 472 (M+H)

Biological Assays

The results of the following assays demonstrate that the compounds Examples 1 and 2 herein are useful EZH2 inhibitors and may be useful in treating cancer. As used herein, "IC$_{50}$" refers to the concentration of an agent which produces 50% of the maximal inhibitory response possible for that agent, (relative IC$_{50}$), or the concentration of an agent which produces 50% inhibition of the target enzyme activity compared to placebo control (absolute $IC_{50}$).

EZH2 WT/Y641N Mut 384-Well Biochemical Assay

The purpose of this assay is to measure the compound effect on the catalytic activity of EZH2 WT/Y641N in the context of the PRC2 complex.

Express FLAG-tagged EZH2 or EZH2 Y641N as the PRC2 5-membered (5-mer) complex consisting of EZH2, EED, SUZ12, RBBP4 and AEBP proteins using a baculovirus expression system in Sf9 cells, and purify using FLAG® Affinity Purification (Sigma-Aldrich). Dilute the enzyme complex into a working stock of 3.33 nM (6.67 nM for mut assay) with Assay Buffer (50 mM Tris-HCl pH 8.5, 10 mM DTT, 0.005% TRITON®-X 100). In the WT assay, dilute non-biotin lysine 27 tri-methylated histone H3 (21-44) co-activator peptide (CPC Scientific Cat #869799) into the above enzyme working solution to a final concentration of 13.33 nM. Co-dilute biotin histone H3 (21-44) peptide substrate (residues 21-44, CPC Scientific Cat#811115) for the WT assay or biotin lysine 27 di-methylated histone H3 (21-44) peptide substrate (CPC Scientific, Cat#830754) for the mut assay with $^3$H-SAM (Adenosyl-L-methionine, S-(methyl)-$^3$H (Adomet), lot 169500/12, 15 Ci/mmol or 0.55 mCi/mL, 36.7 µM, Perkin Elmer NET155) to a final concentration of 4 µM (WT assay) or 2 µM (mut assay) in Assay Buffer.

Add test compounds in 100% DMSO (50 µL of a 4 mM stock for WT assay or 50 µL of a 0.2 mM stock for mut assay) to a 384 well Nunc plate (Thermo Scientific, Cat#264573). Place 20 µL 100% DMSO in dilution wells. Perform 3× serial dilutions by transferring 10 µL from one well to the next. In the WT assay, mix 2 µL of serially diluted compound with 38 µL of DMSO in a Labcyte 384 well plate (Cat# P-05525), whereas in the mut assay, transfer all 20 µL of serially diluted compound to a 384-well Labcyte low volume plate (Cat# LP-0200). 200 nL (WT assay) or acoustically transfer 100 nL (mut assay) compound to a recipient 384-well assay plate (Corning 3706). In the WT assay, dispense 15 µL of the enzyme/tri-methyl H3 co-activator peptide mix into the assay plate, followed by 5 µL of the biotin H3 peptide substrate/$^3$H-SAM mix. Seal the plates and shake for 2 hours at room temperature. Final assay conditions are 2.5 nM enzyme complex, 10 nM tri-methyl histone/co-activator H3 peptide, 1 µM biotin substrate peptide, 1 µM $^3$H-SAM, and test compound at a top concentration of 1 µM (WT assay); or 5 nM enzyme complex, 0.5 µM biotin substrate peptide, 0.5 µM $^3$H-SAM, and test compound at a top concentration of 1 µM (mut assay). Reconstitute Yttrium Silicate Streptavidin SPA beads (Perkin Elmer, Cat# RPNQ0012) at 1 mg/mL (WT assay) or 0.5 mg/mL (mut assay) in 3 M guanidine-HCL. Add the bead mixture to the assay plates at 20 µL per well, shake for 10 minutes, and allow to settle for 1 hour at room temperature prior to counting on a Microbeta. Calculate raw data (CPM) and normalize to % inhibition using Genedata Assay Analyzer as % Inhibition=100−[(Test Compound CPM−Median Min CPM)/(Median Max CPM−Median Min CPM)×100]. Plot normalized data and render curves using Genedata Condoseo as % inhibition (y axis) vs. log compound concentration (x-axis), and determine $IC_{50}$ values using a 4-parameter nonlinear logistic fitting algorithm. Compounds within the scope of the invention are tested in this assay substantially as described above. The compounds of Examples 1 and 2 have biochemical $IC_{50}$ results that demonstrate inhibition of the methyltransferase activity of recombinant WT/mut EZH2 in the context of the PRC2 complex. For example, the compound of Example 1 shows an $IC_{50}$ of 0.93±0.5 nM (n=3) against WT 5-mer EZH2 and 1.43 nM (n=1) against mut 5-mer EZH2. The compound of Example 2 shows an $IC_{50}$ of 6.45 nM (n=1) against WT 5-mer EZH2 and 14.8 nM (n=1) against mut 5-mer EZH2.

H3K27Me3 Cell-Based ELISA

The purpose of this assay is to evaluate the ability of a compound to inhibit the functional activity of EZH2 in cells, via measurement of levels of cell tri-methylated H3K27. Plate MDA MB-231 (EZH2 WT) or Karpas-422 (EZH2 Y641N) cells at 3500/100 µL/well (for MDA MB-231) or 5,000 cells/100 µL/well (for Karpas-422) in black 96-well BD BioCoat Cellware, Poly-Lysine plates (BD Biosciences, Cat#354640). Prepare compound plates in a Nunc™ 96-Well Polypropylene MicroWell Plate (Thermo Scientific Cat# #249944) with the addition of 40 µL/well of 10 mM compound (representing starting final concentration of 20 µM) or 40 µL DMSO, then prepare serial dilutions through the transfer of 20 µL from one well to the next. Add 5 µL of test compound to 245 µL/well of growth media in a separate Nunc™ 96-Well Polypropylene MicroWell Plate, and stamp 11 µL of the compound/media mix onto the cell plates. Place cell plates in a 37° C. incubator for 48 hours. Remove plates from the incubator, place the plates at room temperature for 15-20 minutes, and spin down the plates at 1000 rpm for 5 minutes. Fix cells with 30 µL 16% paraformaldehyde for 15 minutes at room temperature. Remove the paraformaldehyde and permeabilize cells with 100 µL/well PBS minus calcium or magnesium (−/−) containing 0.1% TRITON® X-100 for 20 minutes at room temperature. Wash plates with PBS(−/−) (2×), followed by incubation for 2 hours at room temperature of 50 µL/well of primary antibody solution (Diagenode anti-H3K27me3 MAb-181-050; 1:5000 (for MDA MB-231) or 1:3000 (for Karpas-422) dilution in PBS plus calcium and magnesium (+/+) containing 1% BSA). Wash plates with PBS−/−, (3×) followed by incubation with 50 µL/well secondary antibody solution (Invitrogen goat anti-mouse IgG Alexa 488, Cat# A11001; 1:1000 dilution in PBS+/+) for 1 hour at room temperature in the dark. Wash plates with PBS−/−, (3×), followed by adding 50 µL/well of 5 µg/mL propidium iodide (Invitrogen; Cat# p3566) staining solution in PBS containing 200 µg/mL RNase (Invitrogen; Cat#12091021). Cover plates with black plate seals and scan on Acumen laser scanning cytometer (TTP Lab Tech) with Ex 488 nm/Em 505 nm-530 nm (H3K27m3 signal) and LP655 nm (cell nuclear signal). Compounds within the scope of the invention are tested in this assay substantially as described above. The compound of Example 1 shows a cell H3K27me3 $IC_{50}$s of 1.88±0.66 nM (n=3) or 3.79±1.02 nM (n=4) in MDA MB-231 and Karpas-422, respectively. The compound of Example 2 shows a cell H3K27me3 $IC_{50}$s of 9.02±2.69 nM (n=2) or 144±232 nM (n=2) in MDA MB-231 and Karpas-422, respectively.

Karpas-422 Proliferation Assay

The purpose of this assay is to demonstrate the ability for test compounds to inhibit the growth of tumor cells in vitro.

Plate Karpas-422 cells at a density of 5000 cells/100 µL/well in 96 well, black 96-well BD BioCoat Cellware, Poly-Lysine plates (BD Biosciences, Cat#354640). 40 µL of 10 mM test compound (representing starting final concentration of 20 µM) or add 100% DMSO to a Nunc 96-Well Polypropylene MicroWell Plate (Thermo Scientific Cat# #249944). Perform serial dilutions through the transfer of 20 μL from one well to the next. Add 5 μL of compound to a 245 μL/well of growth media in a separate Nunc 96-Well Polypropylene MicroWell Plate, and stamp 11 μL of the compound/media mix onto the cell plates. Incubate cell plates at 37° C. for 7 days. Add 100 μL/well of Cell Titer GLO® reagent (Promega, Cat# G7671) to the cell plates. Shake 2 minutes and measure luminescence using a plate reader. Compounds within the scope of the invention are tested in this assay substantially as described above. The compound of Example 1 shows an $IC_{50}$ of 49.7±33.9 nM (n=4). The compound of Example 2 shows an $IC_{50}$ of 526 nM (n=1).

Xenograft Studies

The purpose of this assay is to evaluate the ability of a test compound to inhibit tumor EZH2 function and EZH2-mediated tumor growth in vivo.

Conduct in vivo target inhibition and efficacy studies with the compound of Example 1 using the Karpas-422 xenograft model essentially as described in McCabe et al. (2012) Nature 492:108-12, with the following changes/specifications: 1) Use hydroxyethylcellulose (1% HEC/0.25% TWEEN® 80/0.05% antifoam) in place of 20% CAPTISOL® as the formulation vehicle; 2) Administer the compound by oral gavage rather than by intraperitoneal injection; 3) Start compound treatment when tumor volumes reach in range of 200-250 mm$^3$ for efficacy experiments and 300-350 mm$^3$ for target inhibition experiments and; 4) Measure inhibition of tumor methylation or tumor TNFRSF21 expression at day 7 instead of day 10.

ELISA-Based Measurement of Tumor-Derived Tri-Methylated H3K27

To acid-extract histones from tumors, place tumor sections of approximately 0.5 cm by 0.25 cm or 20-30 mg in weight in Lysing Matrix D 500×2 mL Add RNASE/DNASE-free tubes with beads for homogenization (MP Biomedicals, Cat#6913-500). Add 650 μL of Acid Lysis Buffer (0.4 N HCl containing Protease Inhibitor Cocktail Tablets (Roche; Cat#11836153001)). Homogenize tumor samples 2-3 times at speed 6 m/second for 20 seconds in a FastPrep FP120 homogenizer. Set samples on ice for 1 hour to separate. Transfer supernatants to an eppendorf tube and place on a tube rotator to lyse overnight at 4° C. Spin samples down at 8000 rpm for 10 minutes at 4° C. Transfer supernatants to a new tube and measure for protein concentration.

Add 150 μL/well of MSD Blocking Solution A (Meso Scale Discovery (MSD); final concentration of 3%) to a MULTI-SPOT® Tri-Methyl-Histone H3(K27) Singleplex plate (MSD; Cat#: N45CA-1). Shake at room temperature for 1 hour. Wash the plate with 1×MSD Tris Wash Buffer™ (MSD), (3×). Dispense 0.25 μg of tumor lysate in 25 μL Acid Lysis Buffer per well in triplicate. Shake overnight at 4° C. Wash the plate with 1×MSD Tris Wash Buffer™, (3×). Add 25 μL/well of detection antibody SULFO-TAG™-Trimethyl-Histone H3 (K27) diluted to a final concentration of 1.5 μg/μL in Antibody Dilution Buffer (final concentrations of 1% MSD Blocker-A; 0.1% MSD Blocker D-B and 0.1% MSD® Blocker D-G). Shake for 1-2 hours at room temperature. Wash the plate with 1×MSD Tris Wash Buffer, (3×). Fix the plate with the addition of 100 μL/well of 4% formaldehyde in PBS. Shake for 30 minutes at room temperature. Wash the plates with 1×MSD Tris Wash Buffer, (3×). Add 150 μL/well 1×MSD® Read Buffer and measure chemoelectroluminescence using a MSD SECTOR® Imager 6000 instrument. A compound within the scope of the invention is tested in this assay substantially as described above. For example, BID administration in mice of 50 mpk of the compound of Example 1 results in 53% inhibition of tumor methylation (n=8 mice; p<0.0001).

qPCR-Based Measurement of Tumor-Derived TNFRSF21 mRNA Expression

To isolate RNA from tumor tissue, place tumor sections of approximately 0.5 cm by 0.25 cm or 20-30 mg in weight in Lysing Matrix D 500×2 mL Add RNASE/DNASE-free tubes with beads for homogenization (MP Biomedicals, REF: 6913-500). Add 650 μL of RLT buffer from RNeasy® Kit (Qiagen; Cat#74104). Homogenize samples 2 to 3 times at speed 6 for 20 seconds in the FastPrep FP120 homogenizer. Set samples on ice to cool for 10 minutes. Centrifuge at 13 000 rpm for 10 minutes at 4° C. Place supernatants into a QIA tube and isolate RNA using the RNeasy® Kit (Qiagen; Cat#74104).

Prepare cDNA from 3 μg of tumor RNA using the High Capacity cDNA Reverse Transcription Kit (Applied Biosystems; Cat#4368813) and incubate samples in a PCR Thermocycler using the following cycle conditions: 10 minutes at 25° C.; 2 hours at 37° C., hold at 4° C. Amplify cDNA product using Thermo Scientific ABsolute Blue QPCR ROX Mix (Applied Biosystems; Cat# AB-4139) and Taqman probes for TNFRSF21 (Applied Biosystems; Cat# Hs01560899_m1) and housekeeping gene GAPDH (Applied Biosystems; Cat# Hs02758991-g1) in the Applied Biosystems ViiA 7™ Real-Time PCR cycler. Calculate TNFRSF21 cycle threshold values and normalize to its respective sample's GAPDH levels. A compound within the scope of the invention is tested in this assay substantially as described above. For example, BID administration of 50 mpk of the compound of Example 1 results in a 25-fold increase in tumor TNFRSF21 gene expression (n=8 mice; p<0.0001).

The compounds of the present invention are preferably formulated as pharmaceutical compositions administered by a variety of routes. Most preferably, such compositions are for oral administration. Such pharmaceutical compositions and processes for preparing same are well known in the art. See, e.g., REMINGTON: THE SCIENCE AND PRACTICE OF PHARMACY (D. Troy, et al., eds., 21$^{st}$ ed., Lippincott Williams & Wilkins, 2005).

The compounds of the present invention are generally effective over a wide dosage range. For example, dosages per day normally fall within the daily range of about 1 to 1000 mg/day, preferably about 1 to 500 mg/day, administered in one or more doses. It will be understood however that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms.

We claim:

1. A compound selected from the group consisting of:
N-[(4,6-dimethyl-2-oxo-1,2-dihydropyridin-3-yl)
methyl]-5-{(1R)-1-[trans-4-(3-methoxyazetidin-1-yl)
cyclohexyl]ethyl}-4-methylthiophene-3-carboxamide:

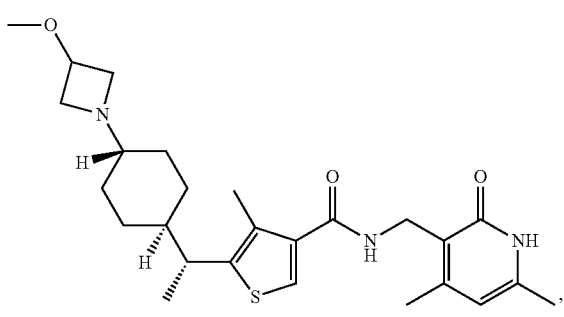

or a pharmaceutically acceptable salt thereof, and
N-[(4,6-dimethyl-2-oxo-1,2-dihydropyridin-3-yl)
methyl]-5-{(1S)-1-[trans-4-(3-methoxyazetin-1-yl)cy-
clohexyl]ethyl}-4-methylthiophene-3-carboxamide:

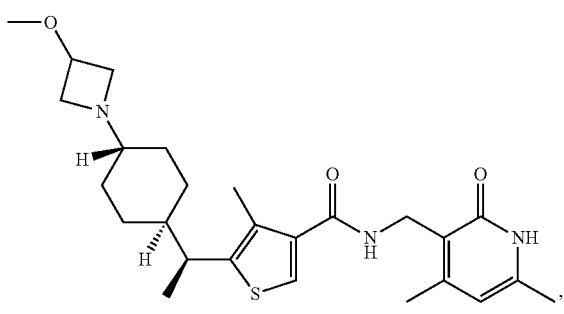

or a pharmaceutically acceptable salt thereof.

2. The compound according to claim 1 which is N-[(4,6-dimethyl-2-oxo-1,2-dihydropyridin-3-yl)methyl]-5-{(1R)-1-[trans-4-(3-methoxyazetidin-1-yl)cyclohexyl]ethyl}-4-methylthiophene-3-carboxamide:

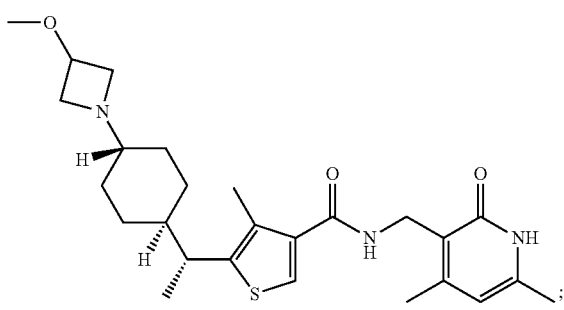

or a pharmaceutically acceptable salt thereof.

3. The compound according to claim 2 which is N-[(4,6-dimethyl-2-oxo-1,2-dihydropyridin-3-yl)methyl]-5-{(1R)-1-[trans-4-(3-methoxyazetidin-1-yl)cyclohexyl]ethyl}-4-methylthiophene-3-carboxamide:

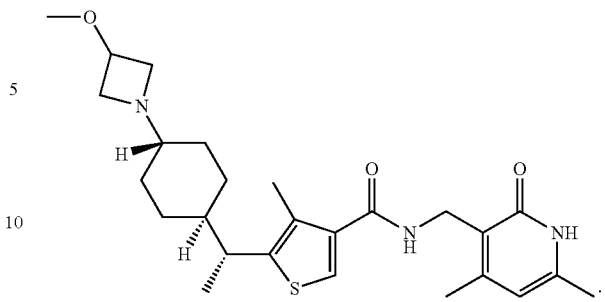

4. A pharmaceutical composition comprising a compound selected from the group consisting of:
N-[(4,6-dimethyl-2-oxo-1,2-dihydropyridin-3-yl)
methyl]-5-{(1R)-1-[trans-4-(3-methoxyazetidin-1-yl)
cyclohexyl]ethyl}-4-methylthiophene-3-carboxamide:

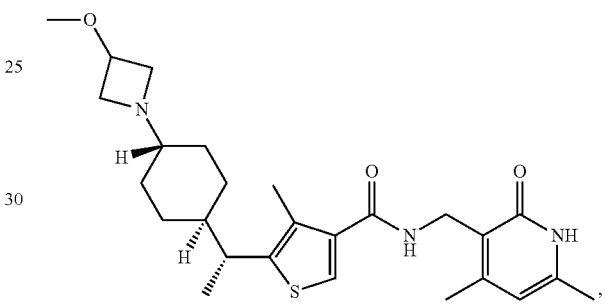

or a pharmaceutically acceptable salt thereof, and
N-[(4,6-dimethyl-2-oxo-1,2-dihydropyridin-3-yl)
methyl]-5-{(1S)-1-[trans-4-(3-methoxyazetin-1-yl)cy-
clohexyl]ethyl}-4-methylthiophene-3-carboxamide:

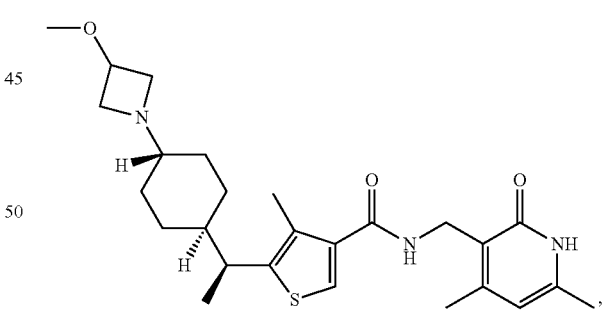

or a pharmaceutically acceptable salt thereof, and one or more pharmaceutically acceptable excipients, carriers, or diluents.

5. A method of treating cancer, wherein the cancer is diffuse large B-cell lymphoma, comprising administering to a patient in need thereof, an effective amount of a compound selected from the group consisting of:
N-[(4,6-dimethyl-2-oxo-1,2-dihydropyridin-3-yl)
methyl]-5-{(1R)-1-[trans-4-(3-methoxyazetidin-1-yl)
cyclohexyl]ethyl}-4-methylthiophene-3-carboxamide:

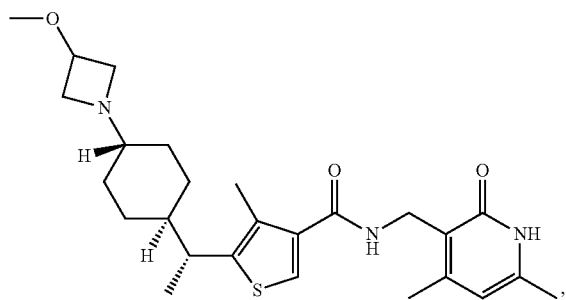
or a pharmaceutically acceptable salt thereof, and N-[(4,6-dimethyl-2-oxo-1,2-dihydropyridin-3-yl)methyl]-5-{(1S)-1-[trans-4-(3-methoxyazetin-1-yl)cyclohexyl]ethyl}-4-methylthiophene-3-carboxamide:
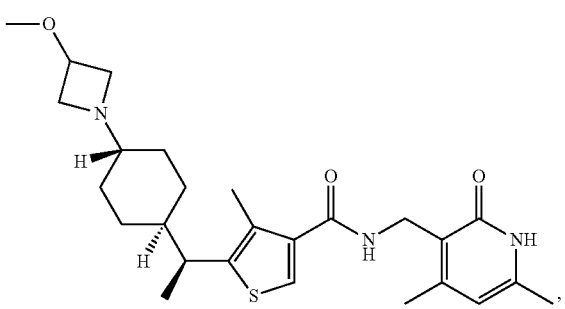
or a pharmaceutically acceptable salt thereof.
* * * * *

UNITED STATES PATENT AND TRADEMARK OFFICE
CERTIFICATE OF CORRECTION

PATENT NO. : 9,527,837 B2
APPLICATION NO. : 14/955074
DATED : December 27, 2016
INVENTOR(S) : Kuo - Long Yu Page 1 of 1

It is certified that error appears in the above-identified patent and that said Letters Patent is hereby corrected as shown below:

In the Specification

At Column 2, Line 43: Please delete the word "methoxyazetin" and insert -- -methoxyazetidin--, therefor.

Signed and Sealed this
Eighteenth Day of April, 2017

Michelle K. Lee
*Director of the United States Patent and Trademark Office*